(12) United States Patent
Hou

(10) Patent No.: US 9,252,366 B2
(45) Date of Patent: Feb. 2, 2016

(54) CROSSLINKABLE COMPOUND, METHOD FOR PREPARING THE SAME AND LIGHT EMITTING DEVICE COMPRISING THE SAME

(71) Applicant: BOE TECHNOLOGY GROUP CO., LTD., Beijing (CN)

(72) Inventor: Wenjun Hou, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 30 days.

(21) Appl. No.: 14/101,824

(22) Filed: Dec. 10, 2013

(65) Prior Publication Data

US 2014/0159014 A1   Jun. 12, 2014

(30) Foreign Application Priority Data

Dec. 11, 2012 (CN) .......................... 2012 1 0535083

(51) Int. Cl.
 C08F 220/24 (2006.01)
 C07C 405/00 (2006.01)
 H01L 51/00 (2006.01)
 C07C 219/32 (2006.01)
 H01L 51/50 (2006.01)

(52) U.S. Cl.
 CPC ............ H01L 51/004 (2013.01); C07C 219/32 (2013.01); H01L 51/0035 (2013.01); H01L 51/5056 (2013.01)

(58) Field of Classification Search
 CPC ..................................................... C07C 219/32
 See application file for complete search history.

(56) References Cited

FOREIGN PATENT DOCUMENTS

JP   2010-021422 A   1/2010
WO  2007/133633 A2   11/2007

OTHER PUBLICATIONS

First Chinese Office Action dated Sep. 29, 2013; Appln. No. 201210535083.5.
Second Chinese Office Action dated Apr. 11, 2014; Appln. No. 201210535083.5.
Extended European Search Report dated Feb. 24, 2014; Appln. No. 13196592.3-1451.

*Primary Examiner* — Yong Chu
*Assistant Examiner* — Ana Z Muresan
(74) *Attorney, Agent, or Firm* — Ladas & Parry LLP

(57) ABSTRACT

A crosslinkable compound comprising trifluorovinyl has a structure of Formula (I). A method for preparing the crosslinkable compound and a light emitting device prepared from the compound are also disclosed.

$$(A)-CH_2-OR \qquad (I)$$

9 Claims, 1 Drawing Sheet

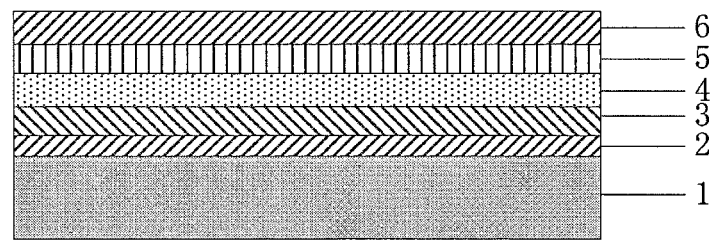

CROSSLINKABLE COMPOUND, METHOD FOR PREPARING THE SAME AND LIGHT EMITTING DEVICE COMPRISING THE SAME

FIELD OF INVENTION

The invention relates to a crosslinkable compound as well as a method for preparing the same and a light emitting device comprising the same.

BACKGROUND OF INVENTION

Liquid crystal display has the advantages such as large screen, high resolution, small and portable, low price and flat screen, etc. However, since the liquid crystal itself cannot emit light, the image has to be displayed relying on a backlight source or ambient light. Thus, the liquid crystal also has the shortcomings such as narrow visual angle, slow response (magnitude of millisecond), and not useful under low temperature, etc. Therefore, people attempt to find a new light emitting material that can replace liquid crystal materials, and thus OLED (Organic Light-Emitting Diodes) and PLED (Polymer Light-Emitting Diodes) have been produced. OLED/PLED has the advantages such as self-illuminating, wide visual angle, high contrast, low power consumption, fast response, full color and simple manufacture, etc.

With the OLED/PLED techniques gradually becoming mature, they have already been used in the filed of flat display, such as some terminal devices like computer, cell phone, and the like. Compared to traditional liquid crystal flat display (TFT-LCD), OLED/PLED displays have the advantages such as lighter and thinner, low power consumption, clear and bright color and wide visual angle.

Generally, OLED/PLED devices have a multilayer structure comprising a hole transport layer (HTL), an emitting layer that converts electric energy to luminous energy, an electron transport layer (ETL), etc. Its mechanism of operation is as follows: under the effect of an external electric field, a hole injected by an anode and an electron injected by a cathode, after passing through the hole transport layer and the electron transport layer, complex with each other in the emitting layer, and interact to produce an activated exciton which will generate an energy difference by radiative transition when it returns to a ground state from an excited state, and finally releases luminous energy in the form of photons. The hole transport layer and the electron transport layer serve to maintain a balance between the injections of the holes and the electrons.

Most of OLED/PLED devices have a sandwich structure. That is, an organic film having semi-conductor properties is sandwiched by electrodes on two sides, and at least one side is a transparent electrode, such as an ITO (indium tin oxide) layer, so as to obtain a planar illumination.

OLED device usually has several organic material layers between the metal cathode and the ITO anode. The device structure is usually formed by evaporation coating one layer by one layer with a vacuum evaporation technique. Evaporation coating has low material utilization, high requirements for devices and is not applicable for large scale production.

In contrast, PLED is manufactured by using a solution procedure, including spin coating and inject printing method. It has the advantages of high material utilization and applicability for manufacture of large scale and large size products. One difficulty of the solution procedure is that the upper layer solution may dissolve the organic molecules which have already formed into a film, thereby affecting the efficiency of the materials and the performance of the device. In order to protect the polymer film already formed from being dissolved into the solvent, the polymer film may be cross-linked to form a polymer network which would not be dissolved by the solvent.

SUMMARY OF INVENTION

In an embodiment of the invention, there is provided a crosslinkable compound comprising trifluorovinyl, which has a structure of Formula (I):

Wherein,

R is a crosslinking group having a structure of formula below,

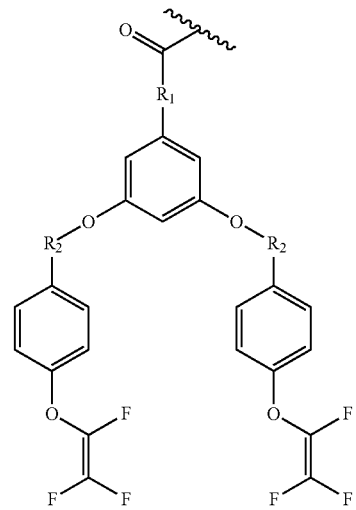

" ⌇ " denotes point of attachment to Formula (I),

A is an aromatic polyamine compound which forms the main structure of a hole transport material, $R_1$ is an alkyl chain having 1-4 carbon atoms, and $R_2$ is an alkyl chain having 1-4 carbon atoms.

In an embodiment of the invention, there is further provided a method for preparing the crosslinkable compound comprising trifluorovinyl, comprising: treating compound A to form an aldehyde, reducing the aldehyde to a hydroxyl containing compound, and esterifying the hydroxyl containing compound with a trifluorovinyl containing crosslinking agent to generate the crosslinkable compound comprising trifluorovinyl; the compound A is an aromatic polyamine compound.

In an embodiment of the invention, there is further provided a light emitting device comprising a hole transport layer which is made from a hole transport material generated by crosslinking and curing the aforesaid crosslinkable compound.

BRIEF DESCRIPTION OF DRAWINGS

FIG. 1 is a schematic diagram of the light emitting device of the invention.

DETAILED DESCRIPTION OF INVENTION

The following embodiments are provided to illustrate the invention, rather than limiting the scope of the invention.

The crosslinkable compound of the invention comprises trifluorovinyl and has a structure of Formula (I):

  (I)

wherein R is a crosslinking group having a structure of formula below,

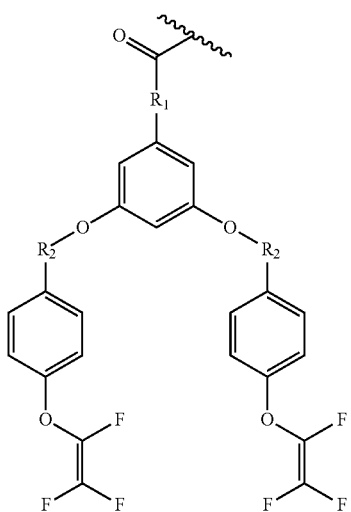

" <span>↝</span> " denotes point of attachment to Formula (I), wherein A is a compound which forms the main structure of a hole transport material, that is, an aromatic polyamine compound. Generally, compound A may be N,N'-diphenyl-N,N'-bis(1-naphthyl)-1,1'-biphenyl-4,4'-diamine (NPD), N,N'-diphenyl-N,N'-bis(3-methylphenyl)-1,1'-biphenyl-4,4'-diamine (TPD), 4,4',4''-tri(N-3-methylphenyl-N-phenylamino)triphenylamine (m-MTDATA), 1,1-bis[(di-4-tolylamino)phenyl]cyclohexane (TAPC), triphenylamine (TPA), N,N'-bis(4-methylphenyl)-N,N'-bis(3-ethylphenyl)-[1,1'-(3,3'-dimethyl)biphenyl]-biphenyl-4,4'-diamine (ETPD), tetra (3-methylphenyl)-N,N N',N'-2,5-diphenylenediamine (PDA), or N,N,N',N'-tetra(4-methylphenyl)-(1,1'-biphenyl)-4,4'-diamine (TTB). For example, compound A may be NPD, TPD or m-MTDATA.

As to the crosslinking group R, $R_1$ is generally an alkyl chain having 1-4 carbon atoms, for example, an alkyl chain having 1-3 carbon atoms, such as —$CH_2$— or —$CH_2$—$CH_2$—. $R_2$ is an alkyl chain having 1-4 carbon atoms, for example, an alkyl chain having 1-3 carbon atoms, such as —$CH_2$— or —$CH_2$—$CH_2$—.

The crosslinkable compound comprising trifluorovinyl may be prepared by the steps of: treating compound A to form an aldehyde, reducing the aldehyde to a hydroxyl containing compound, and esterifying the hydroxyl containing compound with a trifluorovinyl containing crosslinking agent to generate the crosslinkable compound comprising trifluorovinyl.

For example, the method comprises the steps of:
1) reacting compound A with N,N-dimethylformamide at a reaction temperature of 50-70° C. for 3-7 hours, to generate a compound comprising an aldehyde group (Compound A-CHO);

2) reducing the compound comprising an aldehyde group in the presence of a reducing agent at room temperature, to generate a compound comprising a hydroxyl group (Compound A-$CH_2$OH);

3) esterifying the compound comprising a hydroxyl group with a trifluorovinyl-containing crosslinking agent in the presence of 1,3-dicyclohexylcarbodiimide (DCC) at room temperature, to obtain the crosslinkable compound comprising trifluorovinyl.

The reducing agent may be selected from common reducing agents in the art. For example, it may be sodium borohydride and Lithium aluminium hydride.

The trifluorovinyl containing crosslinking agent may be any crosslinking agent of that type known in the art. For example, it may include, but is not limited to 3,5-bis(4-(1,2,2-trifluoroethyleneoxy)benzyloxy)phenylacetic acid, 3,5-bis(4-(1,2,2-trifluoroethyleneoxy)benzyloxy)phenylpropionic acid and 3,5-bis(4-(1,2,2-trifluoroethyleneoxy)phenylethoxy)phenylacetic acid.

For example, the method for preparing the crosslinkable compound comprising trifluorovinyl comprises the steps of:

1) Synthesis of A-CHO

At 0-4° C., under nitrogen protection, 6.0-6.5 g $POCl_3$ is added to 2.5-3.0 g N,N-dimethylformamide (DMF), followed by the addition of 10-20 g Compound A in 120 ml 1,2-dichloroethane and the mixture heated to 50-70° C., for 3-7 hours. After cooling, the reaction mixture is added into 500 ml water, and extracted with ethyl acetate. The organic layer is neutralized with aqueous $NaCO_3$ solution. Isolation is conducted by silica gel chromatography using a petroleum ether/ethyl acetate (with a volume ratio of 10:1) mixed solvent as the developing solvent, to give A-CHO. The yield is 30-65%.

2) Synthesis of A-$CH_2$OH

At room temperature, a solution of 2.0-2.1 g $NaBH_4$ in 5-7 ml MeOH is added to a solution of 5.0-10.0 g A-CHO in 60-100 ml THF. The mixture is stirred for 24 hours at room temperature, and 250 ml water is added. The reaction is extracted with ethyl acetate. After evaporation of solvent, isolation is conducted by silica gel chromatography using a petroleum ether/acetone (with a volume ratio of 8:2) mixed solvent as the developing solvent, to generate A-$CH_2$OH. The yield is 90-98%.

3) Esterification of A-$CH_2$OH with a trifluorovinyl containing crosslinking agent At room temperature, a mixture of 5.0-10.0 g A-$CH_2$OH, 5.0-6.0 g a trifluorovinyl containing crosslinking agent, and 0.2-0.25 g dimethylaminopyridine p-toluenesulfonate (DPTS) in tetrahydrofuran/dichloromethane (30 mL/30 mL) is stirred under $N_2$ protection for 15 min, followed by the addition of 0.6-0.7 g 1,3-dicyclohexylcarbodiimide (DCC) and the mixture reacted at room temperature overnight. After evaporation of solvent, isolation is conducted by silica gel chromatography using a petroleum ether/acetone (with a volume ratio of 8:2) mixed solvent as the developing solvent, to give the final product. The yield is 40-65%.

The crosslinkable compound comprising trifluorovinyl thus prepared can be formed into a hole transport material via crosslinking and curing. The hole transport material then can be formed into the hole transport layer in a light emitting device. Therefore, the invention further provides a hole transport layer made from the hole transport material obtained by crosslinking and curing the crosslinkable compound comprising trifluorovinyl.

When the crosslinkable compound comprising trifluorovinyl is used as the hole transport material of the light emitting device, it firstly forms a film on a substrate such as ITO or silicon slice for example by spin coating or inkjet printing in the form of a solution, and then is subjected to crosslinking and curing to produce the hole transport material, which will form the hole transport layer in the light emitting device.

For example, the hole transport material may be generated by dissolving the crosslinkable compound into an appropriate solvent and heat crosslinking and curing it at 160-200° C. for 5-70 minutes. The solvent used may include but is not limited to toluene, chlorobenzene, o-dichlorobenzene, 1,1-dichloroethane or tetrahydrofuran, and the like.

The cured hole transport material cannot be dissolved in common organic solvents such as methanol, tetrahydrofuran, chloroform, toluene, etc.

Therefore, the invention further provides a light emitting device comprising a hole transport layer formed from a hole transport material generated by crosslinking and curing the crosslinkable compound comprising trifluorovinyl.

The light emitting device may generally comprise an anode, a cathode, a light emitting layer between the anode and the cathode, an electron transport layer between the cathode and the light emitting layer, and a hole transport layer between the anode and the light emitting layer.

For example, the light emitting device of the invention may be placed on a substrate 1 (such as glass, quartz, etc.) and comprises an anode (ITO layer) 2, a cathode layer 6, a light emitting layer 4 between the anode 2 and the cathode 6, an electron transport layer 5 between the cathode 6 and the light emitting layer 4, and a hole transport layer 3 between the anode 2 and the light emitting layer 4, which hole transport layer 3 comprises a hole transport material formed by crosslinking and curing the crosslinkable compound comprising trifluorovinyl, as shown in FIG. 1.

The crosslinkable compound comprising trifluorovinyl of the invention and the hole transport material formed by crosslinking and curing the compound have the following advantages:

1) In the embodiment of the invention, the compound as the main structure of the hole transport layer introduces only one crosslinking group to obtain a good crosslinking effect.

2) The compound of the invention has good solubility, stable chemical properties and good solution processing performance.

3) The heat crosslinking reaction of the compound is a self-crosslinking process without generating any side product, and is strongly responsive to temperature so that the temperature control of the crosslinking reaction is precise.

4) The hole transport material generated after crosslinking and curing the compound will not be dissolved in an organic solvent and thereby not be affected by the solution forming the upper layer.

The following examples are provided to illustrate the process for preparing the crosslinkable compound comprising trifluorovinyl and the light emitting and light emitting device. The examples are used to illustrate the invention only, but are not intended to limit its scope in any way.

EXAMPLE

The reactants represented by the abbreviations in the examples are listed as follows:
DMF: N,N-dimethylformamide;
THF: tetrahydrofuran;
MeOH: methanol;
DCC: 1,3-dicyclohexylcarbodiimide;
DPTS: dimethylaminopyridine p-toluenesulfonate;
$POCl_3$: phosphoryl chloride;
$NaBH_4$: sodium borohydride; and
DCM: dichloromethane.

Example 1

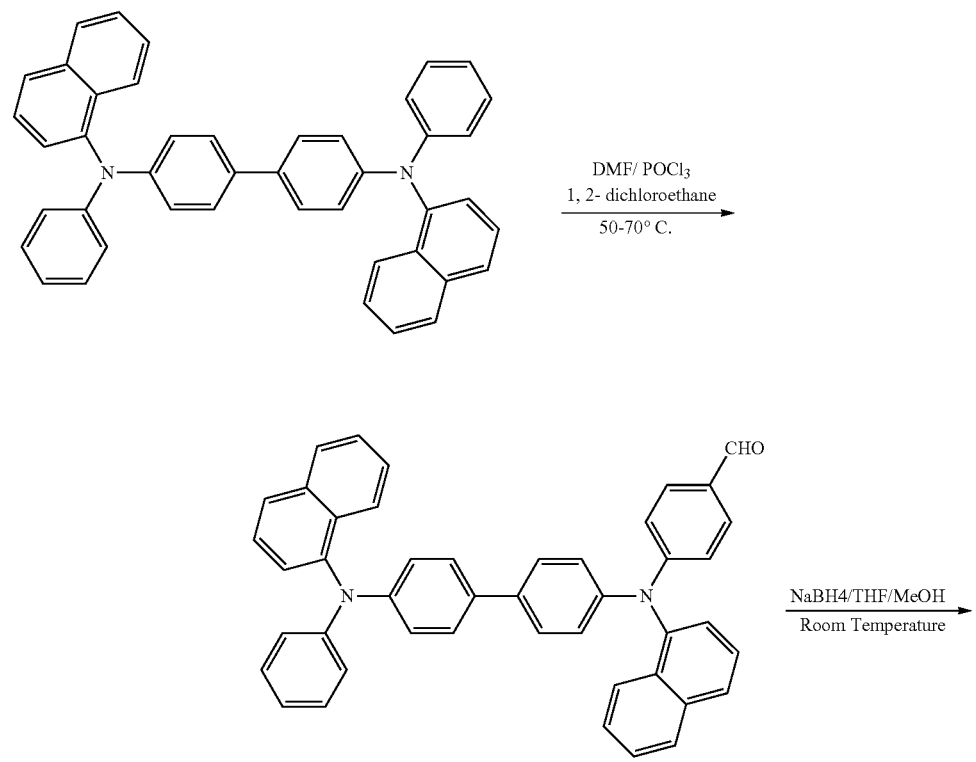

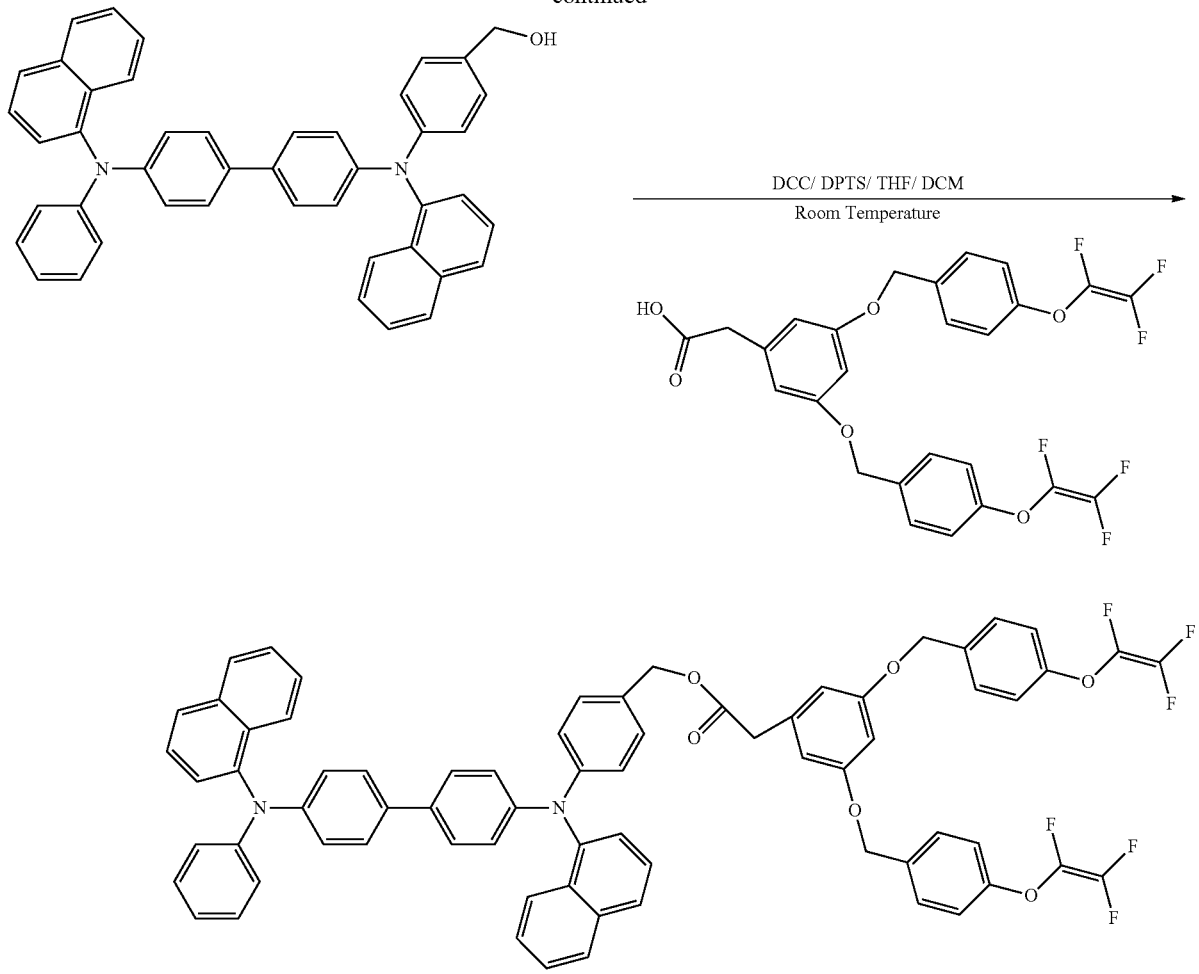

1) Synthesis of NPD-CHO(NPD Comprising an Aldehyde Group)

At 0° C., under nitrogen protection, $POCl_3$ (6.0 g) is added to DMF (2.5 g), followed by the addition of NPD (11.0 g) in 120 ml 1,2-dichloroethane, and the mixture heated to 50° C. for 7 hours. After cooling, the reaction mixture is added into 500 ml water, and extracted with ethyl acetate. The organic layer is neutralized with aqueous $NaCO_3$ solution. Finally isolation is conducted by silica gel chromatography using a petroleum ether/ethyl acetate (with a volume ratio of 10:1) mixed solvent as the developing solvent, to give NPD-CHO, and the yield is 45%.

2) Synthesis of NPD-CH$_2$OH(NPD Comprising a Hydroxylmethyl Group)

At room temperature (15° C.), a solution of $NaBH_4$ (2.0 g) in MeOH (5 ml) is added to a solution of NPD-CHO (5.0 g) in 60 ml THF. The mixture is stirred at room temperature for 24 hours, and 250 ml water is added. The mixture is extracted with ethyl acetate. After evaporation of solvent, isolation is conducted by silica gel chromatography using petroleum ether/acetone (with a volume ratio of 8:2) mixed solvent as the developing solvent, to give NPD-CH$_2$OH, and the yield is 90%.

3) Esterification of NPD-CH$_2$OH with a Trifluorovinyl Containing Crosslinking Agent At room temperature (20° C.), a mixture of NPD-CH$_2$OH (5.0 g), a trifluorovinyl containing crosslinking agent (3,5-bis (4-(1,2,2-trifluoroethyleneoxy)benzyloxy)phenylacetic acid) (5.0 g) and DPTS (0.2 g) in tetrahydrofuran/dichloromethane (30 mL/30 mL) is stirred under $N_2$ protection for 15 min, followed by the addition of DCC (0.6 g), and the mixture reacted at room temperature (15° C.) over night. After evaporation of solvent, isolation is conducted by silica gel chromatography using petroleum ether/acetone (with a volume ratio of 8:2) mixed solvent as the developing solvent, to give 3.5 g NPD-crosslinkable group compound, and the yield is about 40%.

After detection by mass spectrometry, $M^+$ (1139);

$^1$H-NMR (CDCl$_3$), δ (ppm): 3.58 (d, 2H), 5.07 (d, 4H), 5.24 (s, 2H), 6.85-6.93 (d, 1H), 7.10-7.13 (d, 2H), 7.20-7.26 (m, 9H), 7.39-7.48 (d, 6H), 7.53-7.57 (d, 8H), 7.75-7.77 (t, 2H) 8.20-8.23 (t, 2H).

4) Heat Crosslinking

The NPD-crosslinkable group compound thus obtained is dissolved in a 1,1-dichloroethane solvent, to give a 18 g/L solution, which is deposited onto a ITO layer by spin coating at 600 rpm. The solvent is removed and heated to 170° C., with a crosslinking time of 30 min, to get a hole transport material.

The testings confirm that the hole transport material is not dissolved in common organic solvents such as tetrahydrofuran etc., and can be used as a hole transport layer of an electric device.

Example 2
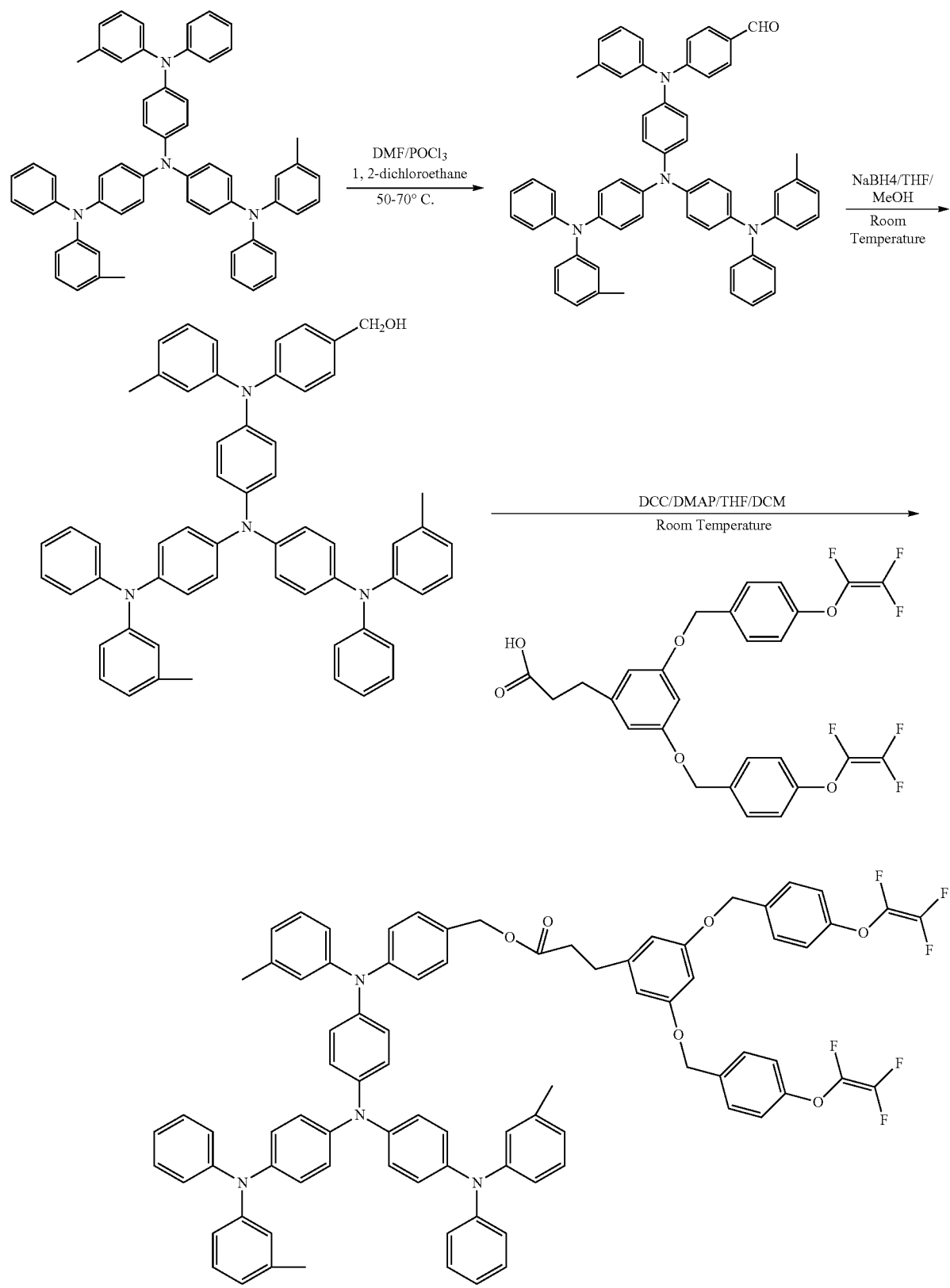

1) Synthesis of m-MTDATA-CHO

At 0° C., under nitrogen protection, $POCl_3$ (6.5 g) is added to DMF (3.0 g), followed by the addition of m-MTDATA (18.0 g) in 120 ml 1,2-dichloroethane and the mixture heated to 60° C. for 5 h. After cooling, the mixture is added into 500 ml water, and extracted with ethyl acetate. The organic layer is neutralized with aqueous $NaCO_3$ solution. Finally isolation is conducted by silica gel chromatography using a petroleum ether/ethyl acetate (with a volume ratio of 10:1) mixed solvent as the developing solvent, to give m-MTDATA-CHO, and the yield is 55%.

2) Synthesis of m-MTDATA-$CH_2OH$

At room temperature (22° C.), a solution of $NaBH_4$ (2.1 g) in MeOH (7 ml) is added to a solution of m-MTDATA-CHO (9.0 g) in 100 ml THF. The mixture is stirred at room temperature for 24 hrs, and 250 ml water is added. The mixture is extracted with ethyl acetate. After evaporation of solvent, isolation is conducted by silica gel chromatography using petroleum ether/acetone (with a volume ratio of 8:2) mixed solvent as the developing solvent, to give m-MTDATA-$CH_2OH$, and the yield is 95%.

3) Esterification of a m-MTDATA-$CH_2OH$ with Trifluorovinyl Containing Crosslinking Group At room temperature (22° C.), a mixture of m-MTDATA-$CH_2OH$ (9.0 g), a trifluorovinyl containing crosslinking agent (3,5-bis(4-(1,2,2-trifluoroethyleneoxy)benzyloxy)phenyl-propionic acid) (6.0 g) and DPTS (0.25 g) in tetrahydrofuran/dichloromethane (30 mL/30 mL) is stirred under $N_2$ protection for 15 minutes, followed by the addition of DCC (0.7 g), and the mixture reacted at room temperature overnight. After evaporation of solvent, isolation is conducted by silica gel chromatography using petroleum ether/acetone (with a volume ratio of 8:2) mixed solvent as the developing solvent, to give 9.2 g m-MTDATA-crosslinkable group compound, and the yield is 65%.

After detection by mass spectrometry, $M^+$ (1353);
$^1$H-NMR ($CDCl_3$), δ (ppm): 2.15 (s, 9H), 2.38 (t, 2H), 3.28 (t, 2H), 5.07 (d, 4H), 6.45-6.57 (d, 27H), 6.69 (d, 3H), 7.02-7.06 (d, 4H), 7.12-7.18 (d, 15H).

4) Heat Crosslinking

The m-MTDATA-crosslinkable group compound thus obtained is dissolved in a o-dichlorobenzene solvent, to give a 10 g/L solution, which is deposited onto a silicon slice by inkjet printing. The solvent is removed and heated to 180° C., with a reaction time of 30 min, to give a hole transport material.

The testings confirm that the hole transport material is not dissolved in common organic solvents such as tetrahydrofuran etc., and can be used as a hole transport layer of an electric device.

Example 3

Synthesis of TPD-Crosslinking Group Compound

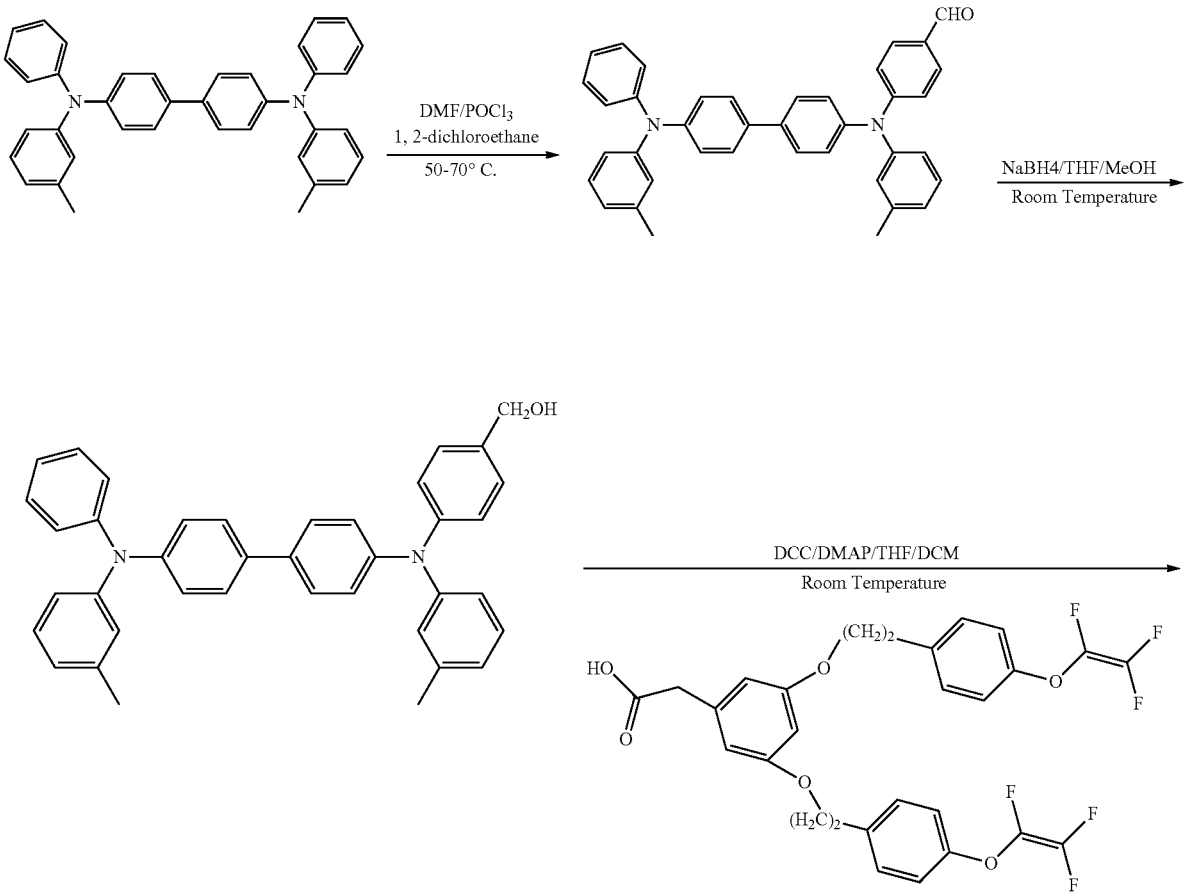

-continued

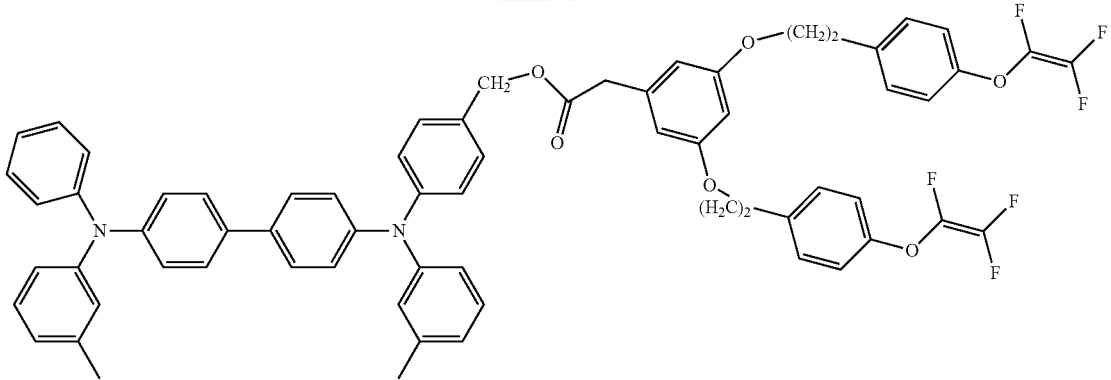

1) Synthesis of TPD-CHO

At 0° C., under nitrogen protection, POCl$_3$ (6.0 g) is added to DMF (2.8 g), followed by the addition of TPD (12.5 g) in 120 ml 1,2-dichloroethane and the mixture heated to 70° C. for 3 h. After cooling, the mixture is added into 500 ml water, and extracted with ethyl acetate. The organic layer is neutralized with aqueous NaCO$_3$ solution. Finally isolation is conducted by silica gel chromatography using a petroleum ether/ethyl acetate (with a volume ratio of 8:1) mixed solvent as the developing solvent, to give TPD-CHO, and the yield is 50%.

2) Synthesis of TPD-CH$_2$OH

At room temperature (25° C.), a solution of NaBH$_4$ (2.1 g) in MeOH (7 ml) is added to a solution of TPD-CHO (6.5 g) in 80 ml THF. The mixture is stirred at room temperature for 24 hrs, and 250 ml water is added. The mixture is extracted with ethyl acetate. After evaporation of solvent, isolation is conducted by silica gel chromatography using petroleum ether/acetone (with a volume ratio of 8:1) mixed solvent as the developing solvent, to give TPD-CH$_2$OH, and the yield is 92%.

3) Esterification of TPD-CH$_2$OH with a Trifluorovinyl Containing Crosslinking Agent At room temperature (22° C.), a mixture of TPD-CH$_2$OH (6.0 g), a trifluorovinyl containing crosslinking agent (3,5-bis (4-(1,2,2-trifluoroethyleneoxy)phenylethoxy)phenylacetic acid) (6.1 g) (6.0 g) and DPTS (0.25 g) in tetrahydrofuran/dichloromethane (30 mL/30 mL) is stirred under N$_2$ protection for 15 minutes, followed by the addition of DCC (0.65 g), and the mixture reacted at room temperature (22° C.) overnight. After evaporation of solvent, isolation is conducted by silica gel chromatography using petroleum ether/acetone (with a volume ratio of 8:2) mixed solvent as the developing solvent, to give 5.3 g TPD-crosslinkable group compound, and the yield is 45%.

After detection by mass spectrometry, M$^+$ (1095);

$^1$H-NMR (CDCl$_3$), δ (ppm): 2.15 (s, 9H), 2.75 (t, 2H), 3.22 (t, 2H), 4.63 (d, 2H), 5.17 (d, 2H), 6.39-6.52 (d, 10H), 6.69 (d, 3H), 7.02-7.06 (d, 4H), 7.53-7.58 (d, 11H), 7.69-7.72 (d, 4H).

4) Heat Crosslinking

The NPD-crosslinkable group compound thus obtained is dissolved in a toluene solvent, to give a 25 g/L solution, which is deposited onto a ITO layer by spin coating at 500 rpm. The solvent is removed and heated to 170° C., with a reaction time of 10 min, to give a hole transport material.

Testings confirm that the hole transport material is not dissolved in common organic solvents such as tetrahydrofuran etc., and can be used as a hole transport layer of an electric device.

By referring to any reaction procedure of Examples 1-3, Compound A such as TAPC, TPA, ETPD, PDA or TTB can be prepared into the corresponding crosslinkable compounds comprising trifluorovinyl, respectively.

Example 4

The process for preparing the light emitting device of the example is shown as follows:

First an anode (ITO layer) 2 is formed on the substrate 1 (such as glass, quartz, etc.).

Then the compounds obtained in Examples 1-3, respectively, are firstly dissolved in a solvent (toluene, chlorobenzene, o-dichlorobenzene, 1,1-dichloroethane or tetrahydrofuran, etc.), and then spin coated onto the ITO layer 2, to give a film with a thickness of 20-80 nm after the evaporation of solvent. The resulting film is subjected to an internal crosslinking reaction at 160-200° C. for 5-70 min, to produce the hole transport layer 3.

The light emitting layer 4 is obtained by spin coating the solution of the upper light emitting layer onto the hole transport layer 3. Since the hole transport layer 3 has already been crosslinked to form a material which is not dissolvable in conventional solvents, the solution of the upper light emitting layer 4 will not dissolve the hole transport layer 3.

Finally, the electron transport layer (LiF) 5 and the cathode (Al) 6 are sequentially obtained by evaporation coating.

The light emitting device thus obtained comprises the following in order: the anode (ITO layer) 2, the hole transport layer 3, the light emitting layer 4, the electron transport layer 5 and the cathode 6, as shown in FIG. 1.

Although the invention has been described in details by way of general illustration, embodiments and experiments, the invention can be modified or changed on such basis, which is apparent to a skilled artisan. Therefore, these modifications or changes, without departing from the spirits of the invention, all fall within the scope of the invention.

What is claimed is:

1. A crosslinkable compound comprising trifluorovinyl represented by a structure of Formula (I):

$$(A)-CH_2-OR \qquad (I)$$

Wherein,

R is a crosslinking group represented by a structure of formula below,

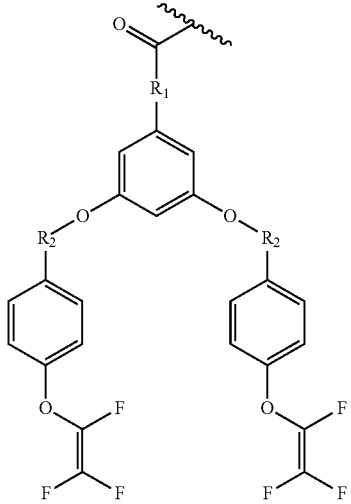

" ∿ " denotes point of attachment to Formula (I),

A is an aromatic polyamine residue which forms the main structure of a hole transport material, wherein (A)-$CH_2$—OR is derived from A-CHO which is obtained by treating an aromatic polyamine, and a point of attachment of (A) to the methylene (—$CH_2$—) group of (A)-$CH_2$—OR is the same as a point of attachment of (A) to the carbonyl group of A-CHO;

$R_1$ is an alkyl chain having 1-4 carbon atoms, and $R_2$ is an alkyl chain having 1-4 carbon atoms.

2. The compound according to claim 1, wherein the aromatic polyamine is selected from the group consisting of N,N'-diphenyl-N,N'-bis(1-naphthyl)-1,1'-biphenyl-4,4'-diamine (NPD), N,N'-diphenyl-N,N'-bis(3-methylphenyl)-1,1'-biphenyl-4,4'-diamine (TPD), 4,4',4''-tri(N-3-methylphenyl-N-phenylamino)triphenylamine (m-MTDATA), 1,1-bis[(di-4-tolylamino)phenyl]cyclohexane (TAPC), triphenylamine (TPA), N,N'-bis(4-methylphenyl)-N,N'-bis(3-ethylphenyl)-[1,1'-(3,3'-dimethyl)biphenyl]-biphenyl-4,4'-diamine (ETPD), tetra(3-methylphenyl)-N,N N',N'-2,5-diphenylenedlamine (PDA), or N,N,N',N'-tetra(4-methylphenyl)-(1,1'-biphenyl)-4,4'-diamine (TTB).

3. The compound according to claim 1, wherein $R_1$ is an alkyl chain having 1-3 carbon atoms, and $R_2$ is an alkyl chain having 1-3 carbon atoms.

4. The compound according to claim 3, wherein $R_1$ and $R_2$ are independently —$CH_2$— or —$CH_2$—$CH_2$—.

5. A method for preparing a crosslinkable compound comprising trifluorovinyl and represented by a structure of Formula (I):

 (I)

Wherein,

R is a crosslinking group represented by a structure of formula below,

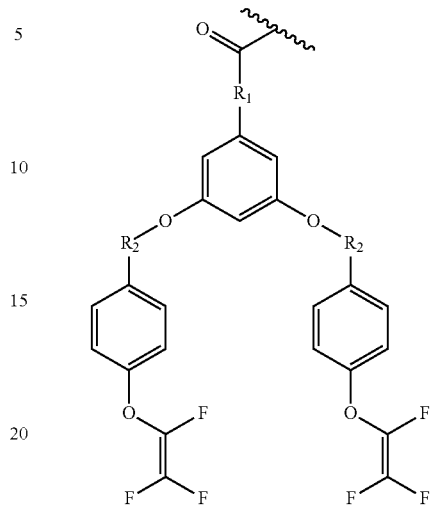

" ∿ " denotes point of attachment to Formula (I),

A is an aromatic polyamine residue which forms the main structure of a hole transport material, wherein (A)-$CH_2$—OR is derived from A-CHO which is obtained by treating an aromatic polyamine, and a point of attachment of (A) to the methylene (—$CH_2$—) group of (A)-$CH_2$—OR is the same as a point of attachment of (A) to the carbonyl group of A-CHO;

$R_1$ is an alkyl chain having 1-4 carbon atoms, and $R_2$ is an alkyl chain having 1-4 carbon atoms, wherein the method comprises: treating the aromatic polyamine to form an aldehyde, reducing the aldehyde to a hydroxyl containing compound, and esterifying the hydroxyl containing compound with a trifluorovinyl containing crosslinking agent to generate the crosslinkable compound comprising trifluorovinyl.

6. The method according to claim 5, wherein the aromatic polyamine is selected from the group consisting of N,N'-diphenyl-N,N'-bis(1-naphthyl)-1,1'-biphenyl-4,4'-diamine (NPD), N,N'-diphenyl-N,N'-bis(3-methylphenyl)-1,1'-biphenyl-4,4'-diamine (TPD), 4,4',4''-tri(N-3-methylphenyl-N-phenylamino)triphenylamine (m-MTDATA), 1,1-bis[(di-4-tolylamino)phenyl]cyclohexane (TAPC), triphenylamine (TPA), N,N'-bis(4-methylphenyl)-N,N'-bis(3-ethylphenyl)-[1,1'-(3,3'-dimethyl)biphenyl]-biphenyl-4,4'-diamine (ETPD), tetra(3-methylphenyl)-N,N N',N'-2,5-diphenylenedlamine (PDA), or N,N,N',N'-tetra(4-methylphenyl)-(1,1'-biphenyl)-4,4'-diamine (TTB).

7. The method according to claim 5, wherein $R_1$ is an alkyl chain having 1-3 carbon atoms, and $R_2$ is an alkyl chain having 1-3 carbon atoms.

8. The method according to claim 7, wherein $R_1$ and $R_2$ are independently —$CH_2$— or —$CH_2$—$CH_2$—.

9. The method according to claim 5, wherein the method comprises the steps of:

1) reacting the aromatic polyamine with N,N-dimethylformamide at a reaction temperature of 50-70° C. for 3-7 hours, to generate Compound A-CHO;

2) reducing A-CHO in the presence of a reducing agent at room temperature, to generate Compound A-$CH_2$OH;

3) esterifying A-$CH_2$OH with a trifluorovinyl containing crosslinking agent in the presence of 1,3-dicyclohexyl-carbodiimide at room temperature, to obtain the crosslinkable compound comprising trifluorovinyl.

* * * * *